(12) United States Patent
Stock

(10) Patent No.: US 6,583,417 B2
(45) Date of Patent: Jun. 24, 2003

(54) INFRARED OPTICAL GAS-MEASURING DEVICE AND GAS-MEASURING PROCESS

(75) Inventor: Burkhard Stock, Lübeck (DE)

(73) Assignee: Drager Sicherheitstechnik GmbH (DE)

( * ) Notice: Subject to any disclaimer, the term of this patent is extended or adjusted under 35 U.S.C. 154(b) by 186 days.

(21) Appl. No.: 09/773,721

(22) Filed: Feb. 1, 2001

(65) Prior Publication Data
US 2001/0015408 A1 Aug. 23, 2001

(30) Foreign Application Priority Data
Feb. 10, 2000 (DE) .......................... 100 05 923

(51) Int. Cl.$^7$ ............................................. G01N 21/00
(52) U.S. Cl. ............................... 250/338.5; 250/339.06
(58) Field of Search ........................ 250/338.5, 339.07, 250/339.08, 343, 339.02, 339.09, 339.13, 338.3, 339.06; 73/19.01, 23.2; 356/437

(56) References Cited

U.S. PATENT DOCUMENTS

| | | | |
|---|---|---|---|
| 3,478,219 A | * 11/1969 | Nutz | 250/208.2 |
| 4,061,918 A | * 12/1977 | Preier et al. | 250/343 |
| 4,740,682 A | * 4/1988 | Frankel | 250/203.1 |
| 4,915,489 A | 4/1990 | Minko | |
| 5,078,473 A | * 1/1992 | McKeown et al. | 359/618 |
| 5,309,921 A | * 5/1994 | Kisner et al. | 600/532 |
| 5,942,755 A | * 8/1999 | Dreyer | 250/339.13 |
| 5,965,887 A | * 10/1999 | Patton | 250/339.09 |
| 5,977,546 A | * 11/1999 | Carlson | 250/339.13 |
| 6,319,375 B1 | * 11/2001 | Warburton | 204/409 |
| 2002/0011568 A1 | * 1/2002 | Diekmann | 250/338.3 |

FOREIGN PATENT DOCUMENTS

| | | |
|---|---|---|
| DE | 36 23 345 A1 | 1/1988 |
| DE | 41 13 795 C1 | 12/1992 |
| DE | 41 33 481 C2 | 8/1993 |
| DE | 43 01 457 A1 | 8/1994 |
| DE | 197 13 928 C1 | 4/1998 |

OTHER PUBLICATIONS

Chelvayohan, Mahesan, "Patented Virtual Reference™ Infrared Gas Sensor" Jul. 1999, pp. 1–6.*

* cited by examiner

Primary Examiner—David Porta
Assistant Examiner—Christine Sung
(74) Attorney, Agent, or Firm—McGlew and Tuttle, P.C.

(57) ABSTRACT

An improved gas-measuring device and a gas-measuring process is provided for determining the concentration of a gas by infrared absorption. The improvement is the compact design of the gas-measuring device and the higher reliability of the measurement results furnished by the gas-measuring device and the gas-measuring process. The gas-measuring device has an infrared radiation source (1), a pyramid-like beam splitter (7), and a quadrant detector, which has two measuring detectors (3, 4) and two reference detectors (5, 6). This guarantees a compact design of the gas-measuring device and, as a consequence, low fault liability of the measurement. The gas-measuring process includes an advantageous evaluation of the measuring signals (M1, M2) received by the two measuring detectors (3, 4) and of the measuring signals (R1, R2) received by the two reference detectors (5, 6). The plurality of the measuring signals (M1, M2, R1, R2) and the manner of their evaluation leads to a more reliable determination of the gas concentration.

16 Claims, 2 Drawing Sheets

INFRARED OPTICAL GAS-MEASURING DEVICE AND GAS-MEASURING PROCESS

FIELD OF THE INVENTION

The present invention pertains to a gas-measuring device for determining the concentration of a gas by the infrared absorption of the measuring signals sent by a radiation source and received by a radiation detector, and to a gas-measuring process for determining the concentration of a gas by the infrared absorption of the measuring signals sent by an infrared radiation source and received by a quadrant detector comprising two measuring detectors and two reference detectors.

BACKGROUND OF THE INVENTION

Such gas-measuring devices and gas-measuring processes have been known from various publications and are used, among other things, for monitoring the air quality, detecting air pollutants, for measuring the concentrations of gases, e.g., carbon dioxide, methane, laughing gas, or for determining the alcohol concentration in the breath of a person.

The infrared radiation passing through the gases to be measured is now attenuated by absorption in a gas-specific manner in certain wavelength ranges. The intensity of the absorption is determined by measurement. It depends on the concentration of the gas, the path length of the radiation and other influential factors such as the temperature, the contamination of mirrors and windows or other beam shields, which, not being due to the gas, shall be left out of consideration during the concentration measurement.

An infrared optical gas-measuring device for determining the concentration of a gas comprises, in principle, a radiation source and a radiation detector. The radiation source sends measuring signals in the infrared wavelength range; these measuring signals pass through the gas to be measured, and are partly absorbed by the gas and are received at a reduced intensity by the radiation detector. The reduction in the intensity is an indicator of the gas concentration.

It has been known that two radiation detectors are used in infrared optical devices for compensating intensity reductions of the measuring signals in the infrared wavelength range, which reductions are not due to the gas. While the first detector measures only radiation from a wavelength range in which the gas, whose concentration is to be measured, has an absorption, the second detector is sensitive only to radiation from a spectral range in which the gas does not absorb. The quotient of these two measuring signals changes only if the gas to be detected is present in the gas-measuring path. Aging effects and other changes in the radiation intensity which do not depend on the spectrum normally affect both radiation detectors equally, so that the quotient remains constant in these cases. However, drifts, which are caused by the contamination of the beam path, may occur even in the case of a design with two radiation detectors. Contaminants are, in general, not distributed homogeneously over the beam cross section, so that the spatial radiation intensity distribution over the cross section of the optical system changes. In connection with the remaining asymmetry in the splitting of the radiation between two detectors, this leads to a change in the quotient, i.e., to a drift in the measurement result of the gas-measuring device.

A measuring device of this type has been known from DE 197 13 928 C1. The concentration of gases is determined there by infrared absorption with two identical radiation sources and two radiation detectors, one of which is used as a measuring detector and the other as a reference detector. Due to this and to the use of optical concentrators for bundling the radiation, stable measured values are obtained despite the contamination or the radiation shielding of the optical surfaces exposed to the gases or gas mixtures.

The drawback of these and other infrared optical gas-measuring devices of this type is the large amount of material needed and the large space requirement as well as the great effort needed for adjustment as a consequence of the mechanical tolerances of the optical requirements.

A multispectral sensor with which different spectral ranges of a radiation to be measured are determined has been known from DE 41 33 481 C2. The multispectral sensor is characterized by small dimensions and high reliability of operation. These advantageous properties are guaranteed by a highly reflecting optical beam-splitting device, which splits the light via a plurality of filters of different spectral transmission ranges among radiation-sensitive elements arranged behind them.

The drawback of this multispectral sensor is that it has no precautionary measures to compensate non-gas-related changes in intensity. Distortions of the measured results cannot therefore be ruled out.

SUMMARY AND OBJECTS OF THE INVENTION

The basic object of the present invention is therefore to provide a compact infrared optical gas-measuring device and a gas-measuring process which furnish reliable measured results for the concentration determination despite disturbances occurring in the path of the radiation.

According to the invention a gas-measuring device is provided for determining the concentration of a gas by the infrared absorption of the measuring signals sent by a radiation source and received by a radiation detector. The radiation source is a infrared radiation source. The radiation detector is a quadrant detector, which comprises four individual detectors arranged in a square pattern. A pyramid-like beam splitter divides the measuring signals of the infrared radiation source among the four individual detectors. The four individual detectors comprise two measuring detectors located opposite one another and two reference detectors located opposite one another. The measuring detectors are equipped with first identical infrared filters and the reference detectors are equipped with second identical infrared filters.

The gas-measuring process for determining the concentration of a gas by the infrared absorption of the measuring signals sent by an infrared radiation source and received by the quadrant detector comprising two measuring detectors and two reference detectors includes forming the quotients:

$$Q1 = \frac{M1}{R1}, Q2 = \frac{M1}{R2}, Q3 = \frac{M2}{R1}, Q4 = \frac{M2}{R2},$$

from the measured signals M1, M2 received by the measuring detectors and the measuring signals R1, R2 received at the reference detectors and using the formed quotients to determine the gas concentration.

An essential advantage of the gas-measuring device according to the present invention is that due to the use of a pyramid-like beam splitter, the measuring signals of an infrared radiation source are divided among four individual detectors, doing so in a compact design with only few components. As a result, the gas-measuring device can be accommodated in a smaller housing. This leads to increased stability with respect to thermal or mechanical stress and is advantageous under real conditions of use when the gas-measuring device is subject to great temperature variations or shocks.

Another advantage arises from the measuring signals received by the four individual detectors. The evaluation of four signals guarantees higher reliability than that of two signals during the measurement of the gas concentration because of a lower probability of false alarms due to the exceeding of preset concentration values when optical components are in reality only partially contaminated or partial components of the gas-measuring device fail.

It is advantageous in the gas-measuring process according to the present invention that four measuring signals are evaluated and that spatially inhomogeneous reductions in the radiation intensity can be detected and are thus taken duly into account for the determination of the gas concentration.

The present invention will be described below as an example based on the schematic drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
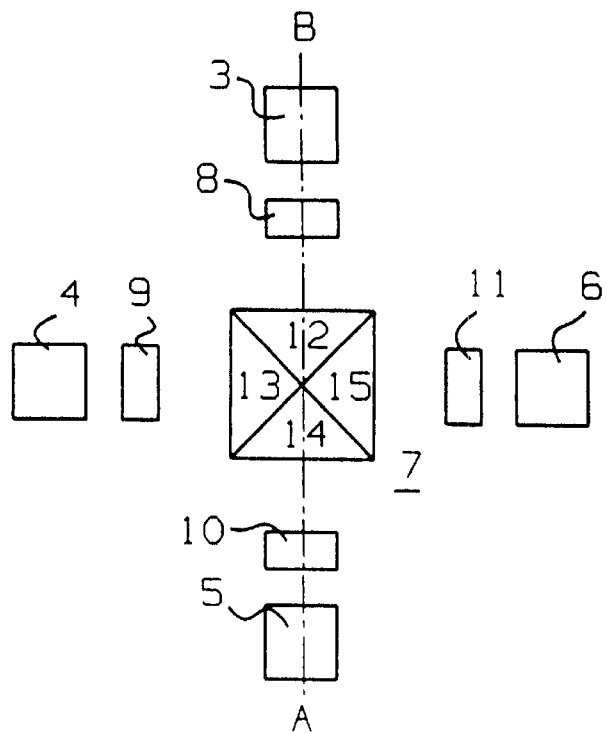
FIG. 1 is a schematic view of the pyramid-like beam splitter and of the quadrant detector from the direction of the incident infrared ray.

Referring to the drawings in particular, FIG. 1 shows a view of the pyramid-like beam splitter 7 and of the quadrant detector from the direction of the incident infrared beam, so that all four individual detectors 3, 4, 5, 6 are visible.

Figure 2:
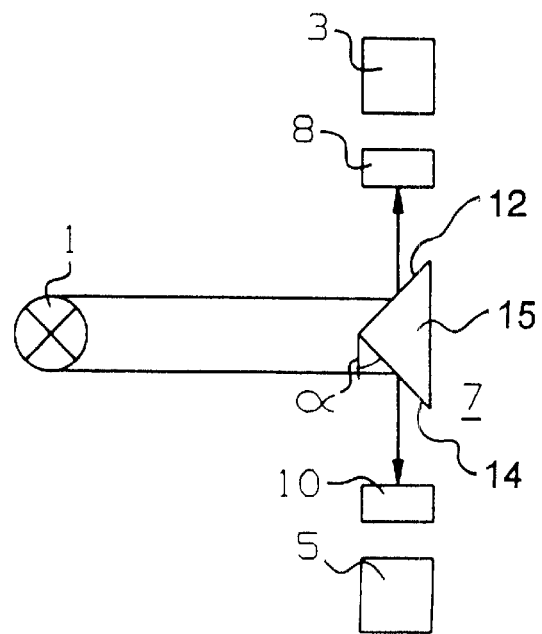
FIG. 2 is a schematic view along section A-B in FIG. 1.

As can be seen in FIGS. 1 and 2 the incident light beam of the infrared radiation source 1 falls, after passing through a gas to be measured, on a pyramid-like beam splitter 7 with square base and with the generated surfaces 12, 13, 14, 15 which faces the light beam at an angle of $\alpha=45°$ and on which the light beam is reflected and split among four individual detectors 3, 4, 5, 6 of the quadrant detector. The individual detectors 4, 6 and generated surface 13 are not visible in FIG. 2 because they are located above or below the plane of the drawing and are covered by the beam splitter 7.

The four individual detectors 3, 4, 5, 6 according to FIG. 1 are arranged in a square-shaped pattern around the pyramid-like beam splitter 7 and comprise the two measuring detectors 3, 5 and the reference detectors 4, 6 located opposite one another. The measuring detectors 3, 5 are equipped with first identical infrared filters 8, 10 and the reference detectors 4, 6 are equipped with two identical infrared filters 9, 11. The infrared filters 8, 10, on the one hand, and 9, 11, on the other hand, have different transmission ranges, outside of which they have strong reflection. The spectral part of the light beam located in the transmission range of the first infrared filters 8, 10 therefore reaches the measuring detectors 3, 5 and the spectral component of the light beam located in the transmission range of the second infrared filters 9, 11 reaches the reference detectors 4, 6.

Figure 3:
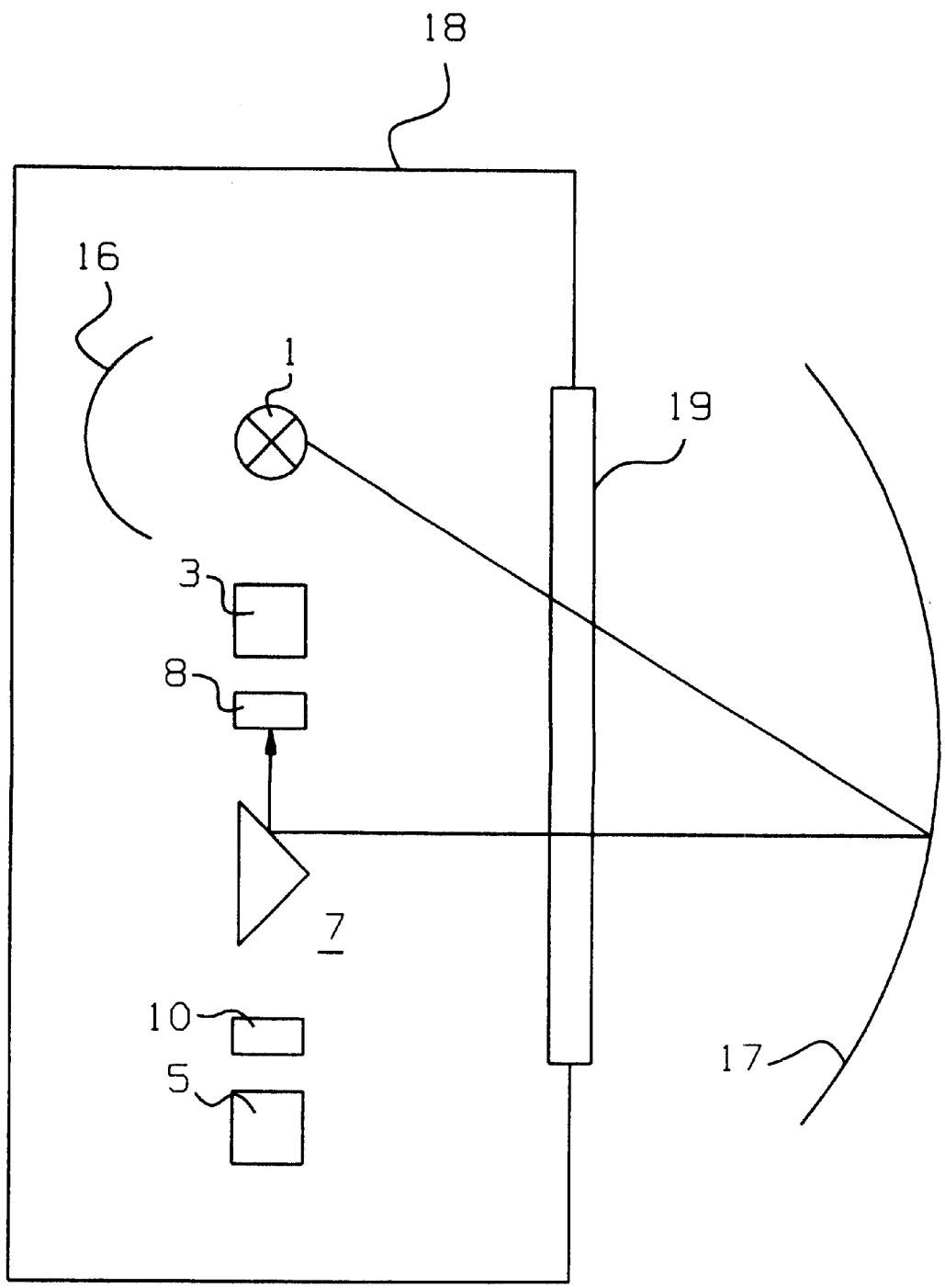
FIG. 3 is a schematic view of the entire gas-measuring device with infrared radiation source, mirrors, pyramid-like beam splitter and quadrant detector.

FIG. 3 shows the entire gas-measuring device in a view at right angles to the incident light beam. The light of an infrared radiation source 1 is bundled with a first mirror 16 into a light beam. The path of the beam corresponding to the bundling is not shown in FIG. 3 for clarity's sake. The light beam subsequently falls on a second mirror 17 and is passed on from there to the pyramid-like beam splitter 7 and farther to the quadrant detector. The infrared radiation source 1, the beam splitter 7 and the quadrant detector are usually located in a housing 18 for protection from contamination with a window 19 for the exit and entry of the light beam. The path traveled by the light beam between the exit point at the window 19 of the housing 18 and the mirror 17 and the path traveled by the light beam between the mirror 17 and the point of entry at the window 19 of the housing 18 form together the measuring section over which the light beam travels in the gas volume of the gas to be measured, which can be detected by the wavelength-dependent absorption of the infrared light in the manner characteristic of this gas.

Depending on the concentration of the gas to be detected, the infrared light is absorbed in the characteristic wavelength range. If the gas to be detected is present at an increased concentration, the measuring signals M1 and M2 received by the measuring detectors 3, 5 decrease, and the measuring signals R1 and R2 received by the reference detectors 4, 6 remain unaffected, because while the measuring signals M1 and M2 are associated with the characteristic wavelength range of the gas to be measured and pass unhindered through the first infrared filters 8, 10 in the transmission range of these filters and their intensity is attenuated by the gas during absorption, the measuring signals R1 and R2 are associated with a wavelength range that is different from this. They pass unhindered through the second infrared filters 9, 11 in the transmission range of these filters, they are not absorbed by the gas and their intensity does not decrease due to absorption.

It follows from the above considerations that the quotient of the measuring signals M1, M2 received at the measuring detectors 3, 5 and the measuring signals R1, R2 received at the reference detectors is an indicator of the gas concentration present.

There are four possibilities of forming a quotient in this case:

$$Q1 = \frac{M1}{R1}, Q2 = \frac{M1}{R2}, Q3 = \frac{M2}{R1}, Q4 = \frac{M2}{R2},$$

The gas concentrations C1, C2, C3, C4, which are determined as follows, are obtained from the quotients Q1, Q2, Q3, Q4 by standardization:

$$C1 = \frac{Q°1 - Q1}{Q°1} \cdot Cal1, C2 = \frac{Q°2 - Q2}{Q°2} \cdot Cal2,$$

$$C3 = \frac{Q°3 - Q3}{Q°3} \cdot Cal3, C4 = \frac{Q°4 - Q4}{Q°4} \cdot Cal4.$$

Q°1, Q°2, Q°3 and Q°4 are quotients of the type mentioned at the beginning, which are calculated for a known gas, a so-called zero gas.

Cal 1, Cal 2, Cal 3 and Cal 4 are calibration factors, which are determined by performing measurements on the gas to be detected later at a known concentration, the so-called reference gas, and calculating the quotients Q1, Q2, Q3, Q4 and the gas concentrations C1, C2, C3, C4 for this. The calibration factors Cal 1, Cal 2, Cal 3, Cal 4 are then obtained as unknowns from the above equations.

In a subsequent measurement with an unknown gas concentration, the gas concentrations C1, C2, C3, C4 are assumed to be equal within certain limits, because it can be assumed that the gas concentration to be measured is distributed homogeneously over the infrared light beam and thus all individual detectors 3, 4, 5, 6 are exposed to the radiation in the same manner during the calibration.

Contaminants distributed inhomogeneously over the radiation cross section, such as dust or water drops, may occur at the window 19 or the mirror 17 during practical applications, and lead to a deviating irradiation of the individual detectors 3, 4, 5, 6 compared with the conditions prevailing during the calibration. This in turn causes that different gas concentrations C1, C2, C3, C4 will be measured.

If all values of the gas concentrations C1, C2, C3, C4 are still within a preset tolerance range, the mean value
C=0.25(C1+C2+C3+C4)
is formed, which shall be used as a valid measured value for the gas concentration to be determined. If at least one of the gas concentrations C1, C2, C3, C4 is outside the preset tolerance, the mean value C can no longer be determined reliably as a valid measured value for the gas concentration. For example, a fault indication may take place, instead.

The selection of the tolerance range depends on many factors, e.g., the signal-to-noise ratio, the response time during the measurement, the required warning thresholds and the required accuracy of the measurement. The tolerance range shall therefore be determined individually for each specific application.

The measurement of methane in plants with explosion hazard, e.g., a drilling platform, represents an exemplary embodiment of a gas-measuring device according to the present invention and of a gas-measuring process. Methane shows a strong absorption in the wavelength range of 3.3 $\mu$m (micrometers) and can be easily detected by infrared optical measurement. The mirror 17 and the window 19 of the housing 18 are preferably spaced at a distance of 8 cm from one another. The measuring path traveled by the light beam in the gas volume is 16 cm. As a result, a compromise has been made between the smallest possible size of the gas-measuring device according to FIG. 3 and a sufficiently long measuring path for the measurement of the light absorption. The infrared filters 8, 10 in front of the measuring detectors 3, 5 are optical interference filters with a central wavelength of 3.3 $\mu$m and a full width of half-maximum of 0.1 $\mu$m and are adapted concerning their transmission range to the wavelength range of the gas absorption. The infrared filters 9, 11 in front of the reference detectors 4, 6 are optical interference filters with a central wavelength of 3.9 $\mu$m and a full width of half-maximum of 0.1 $\mu$m, i.e., their transmission range is outside the characteristic wavelength range of the absorption by methane.

The measurement of the measuring signals M1, M2 received by the measuring detectors 3, 5 and of the measuring signals R1, R2 received by the reference detectors 4, 6 and the subsequent formation of the quotients Q1, Q2, Q3, Q4 is necessary in order to compensate non-gas-related changes in the changes in the radiation intensity detected by the individual detectors 3, 4, 5, 6, e.g., those occurring because of a change in the output of the infrared radiation source 1 or because of a change in the reflection behavior of the mirrors 16, 17. The measuring detectors 3, 5 and the reference detectors 4, 6 are affected by this in the same manner and the quotients Q1, Q2, Q3, Q4 remain unchanged.

The gas-measuring device must be calibrated before the gas measurement proper. To do so, zero gas, preferably clean air or nitrogen, is first admitted into the gas-measuring device, and the quotients Q°1, Q°2, Q°3, Q°4 are determined. Q°1 =Q°2=Q°3=Q°4=1 is assumed in this case for simplicity's sake, i.e., no radiation is absorbed by the zero gas in the relevant wavelength range, but both the measuring signals (M1, M2) and the measuring signals (R1, R2) are received equally without a reduction in their intensity.

A reference gas is subsequently admitted into the gas-measuring device. A gas concentration of 40% of the LEL, i.e., 40% of the Lower Explosion Limit, is usually selected for methane. 100% of the LEL corresponds to 5 vol. % or 50,000 ppm in the case of methane. Experience has shown that this gas concentration attenuates the measuring signals M1, M2 received by the measuring detectors 3, 5 by 12% compared with the unaffected measuring signals R1, R2 received by the reference detectors 4, 6. Therefore, the following value is obtained for the quotients Q1, Q2, Q3, Q4:
Q1=Q2=Q3=Q4=(1−0.12)/1=0.88.
A gas-measuring device usually indicates the gas concentrations C1, C2, C3, C4 in units of the LEL, so that the calibration factors Cal 1, Cal 2, Cal 3, Cal 4 are determined here from the equations:

$$C1 = \frac{Q°1 - Q1}{Q°1} \cdot Cal1, C2 = \frac{Q°2 - Q2}{Q°2} \cdot Cal2,$$

$$C3 = \frac{Q°3 - Q3}{Q°3} \cdot Cal3, C4 = \frac{Q°4 - Q4}{Q°4} \cdot Cal4.$$

in which
C1=C2=C3=C4=40% in % of the LEL,
Q°1=Q°2=Q°3=Q°4=1,
Q1=Q2=Q3=Q4=0.88.
From this we obtain:
Cal1=Cal2=Cal3=Cal4=333.33.
If the gas-measuring device is later used to monitor and determine unknown methane concentrations, the permissible error limit is normally 10% of the measured value, and a fixed value of 4% of the LEL applies at levels below 40% of the LEL. Consequently, the gas concentrations C1, C2, C3, C4 may be between 36% and 44% of the LEL during checking during operation with a reference gas having a concentration corresponding to 40% of the LEL.

Let us now assume such a contamination of the window 19 of the housing 18 of the gas-measuring device that the measuring signals M1, M2, R1, R2 received by the individual detectors 3, 4, 5, 6 will decrease in the following manner compared with the earlier measurement without contamination:
M1 by 5%, M2 by 7%, R1 by 4%, R2 by 3%.
The following values will now be obtained for the quotients Q1, Q2, Q3, Q4:
Q1=0.95/0.96=0.989,
Q2=0.95/0.97=0.979,
Q3=0.93/0.96=0.968,
Q4=0.93/0.97=0.958;
and the following concentrations will be obtained for the gas concentrations C1, C2, C3, C4:
C1=(1−0. 989/1)·333.33=3.66% of the LEL,
C2=(1−0.979/1)·333.33=6.99% of the LEL,
C3=(1−0.968/1)·333.33=10.66% of the LEL,
C4=(1−0.958/1)·333.33=13.99% of the LEL,
and
C=8.82% of the LEL
is obtained for the mean value C.

Thus, not all of the gas concentrations C1, C2, C3, C4 are within the tolerance range of 8.82% of the LEL ±4% of the LEL. Consequently, the calculation of the mean value C as a measured value for the gas concentration makes no sense, and a fault indication should take place, instead.

While a specific embodiment of the invention has been shown and described in detail to illustrate the application of the principles of the invention, it will be understood that the invention may be embodied otherwise without departing from such principles.

What is claimed is:

1. A gas-measuring device for determining the concentration of a gas, comprising:

an infrared radiation source sending measuring signals;

a quadrant radiation detector for infrared absorption of the measuring signal comprising four individual detectors arranged in a square pattern, a pyramid-like beam splitter dividing the measuring signals of the infrared radiation source among said four individual detectors, said four individual detectors including two measuring detectors located opposite one another and equipped with first identical infrared filters and two reference detectors located opposite one another, and equipped with second identical infrared filters.

2. A gas-measuring device in accordance with claim 1, wherein said four individual detectors are pyroelectric detectors.

3. A gas-measuring device in accordance with claim 1, wherein said detectors determine concentration of methane.

4. A gas-measuring device in accordance with claim 1, wherein the transmission range of the infrared filters is 3.3±0.1 $\mu$m.

5. A gas-measuring device in accordance with claim 1, wherein the transmission range of the infrared filters is (3.9±0.1) $\mu$m.

6. A gas-measuring device in accordance with claim 1, further comprising:

a processor for forming the quotients $$Q1 = \frac{M1}{R1}, Q2 = \frac{M1}{R2}, Q3 = \frac{M2}{R1}, Q4 = \frac{M2}{R2},$$

from the measured signals M1, M2 received by the measuring detectors and the reference signals R1, R2 received by the reference detectors and using the formed quotients to determine the gas concentration.

7. A gas-measuring device in accordance with claim 6, wherein:

said processor averages all four formed quotients to determine the gas concentration.

8. A gas-measuring process for determining the concentration of a gas by the infrared absorption of the measuring signals sent by an infrared radiation source and received by a quadrant detector comprising two measuring detectors and two reference detectors, the process comprising the steps of:

forming the quotients $$Q1 = \frac{M1}{R1}, Q2 = \frac{M1}{R2}, Q3 = \frac{M2}{R1}, Q4 = \frac{M2}{R2},$$

from the measured signals M1, M2 received by the measuring detectors and the reference signals R1, R2 received by the reference detectors; and using the formed quotients to determine the gas concentration.

9. A gas-measuring process in accordance with claim 8, wherein the gas concentrations $$C1 = \frac{Q°1 - Q1}{Q°1} \cdot Cal1, C2 = \frac{Q°2 - Q2}{Q°2} \cdot Cal2,$$

$$C3 = \frac{Q°3 - Q3}{Q°3} \cdot Cal3, C4 = \frac{Q°4 - Q4}{Q°4} \cdot Cal4.$$

are obtained from the quotients Q1, Q2, Q3, Q4 by standardization, wherein the quotients Q°1, Q°2, Q°3, Q°4 are related to a zero gas measurement and Cal 1, Cal 2, Cal 3, Cal 4 are calibration factors, which are determined by the measurement of a reference gas.

10. A gas-measuring process in accordance with claim 9, wherein the gas concentrations C1, C2, C3, C4 are determined continuously or at predetermined time intervals.

11. A gas-measuring process in accordance with claim 9, wherein a value is determined for the median for all values of the gas concentrations C1, C2, C3, C4 within a preset tolerance range, and a warning signal is sent if at least one value of the gas concentrations C1, C2, C3, C4 is outside the preset tolerance range.

12. A gas-measuring process in accordance with claim 9, wherein the mean value C=0.25 (C1+C2+C3+C4) is formed for all values of the gas concentrations C1, C2, C3, C4 within a preset tolerance range, and a warning signal is sent if at least one value of the gas concentrations C1, C2, C3, C4 is outside the preset tolerance range.

13. A gas-measuring process in accordance with claim 9, wherein clean air or nitrogen is used as the zero gas for the zero gas measurement.

14. A gas-measuring process in accordance with claim 9, wherein methane with a concentration of 40% of the LEL is used as the reference gas.

15. A gas-measuring process in accordance with claim 8, wherein the concentration of methane is determined.

16. A gas-measuring process in accordance with claim 8, wherein:

said using of the formed quotients to determine the gas concentration includes averaging all four formed quotients.

* * * * *